United States Patent [19]

Elia

[11] Patent Number: 5,372,503

[45] Date of Patent: Dec. 13, 1994

[54] METHOD FOR INSTALLATION OF A DENTAL IMPLANT

[75] Inventor: James P. Elia, Scottsdale, Ariz.

[73] Assignees: Dental Marketing Specialists, Inc., Scottsdale; Jerry W. Bains and Salee C. Baines Irrevocable Trust, Carefree, both of Ariz. ; a part interest

[21] Appl. No.: 53,886

[22] Filed: Apr. 27, 1993

[51] Int. Cl.$^5$ ............................. A61C 5/00; A61C 8/00
[52] U.S. Cl. ...................................... 433/215; 433/173
[58] Field of Search .................... 433/173, 176, 201.1, 433/215

[56] References Cited

U.S. PATENT DOCUMENTS

| | | | |
|---|---|---|---|
| 4,702,697 | 10/1987 | Linkow | 433/173 |
| 4,713,006 | 12/1987 | Hakamatsuka et al. | 433/201.1 |
| 4,728,570 | 1/1988 | Ashman et al. | 428/327 |
| 4,738,623 | 4/1988 | Driskell | 433/173 |
| 4,976,736 | 12/1990 | White | 623/16 |
| 5,002,488 | 3/1991 | Homsy | 433/169 |
| 5,037,442 | 8/1991 | Wintermantel et al. | 623/23 |
| 5,051,091 | 9/1991 | Rosenfeld | 433/201.1 |
| 5,221,204 | 6/1993 | Kruger et al. | 433/173 |

*Primary Examiner*—Gene Mancene
*Assistant Examiner*—Cindy A. Cherichetti
*Attorney, Agent, or Firm*—Tod R. Nissle

[57] ABSTRACT

An implant is loosely inserted in an opening in the bone. A packing composition and/or growth factor is inserted in the opening to anchor the implant in the opening.

8 Claims, 9 Drawing Sheets

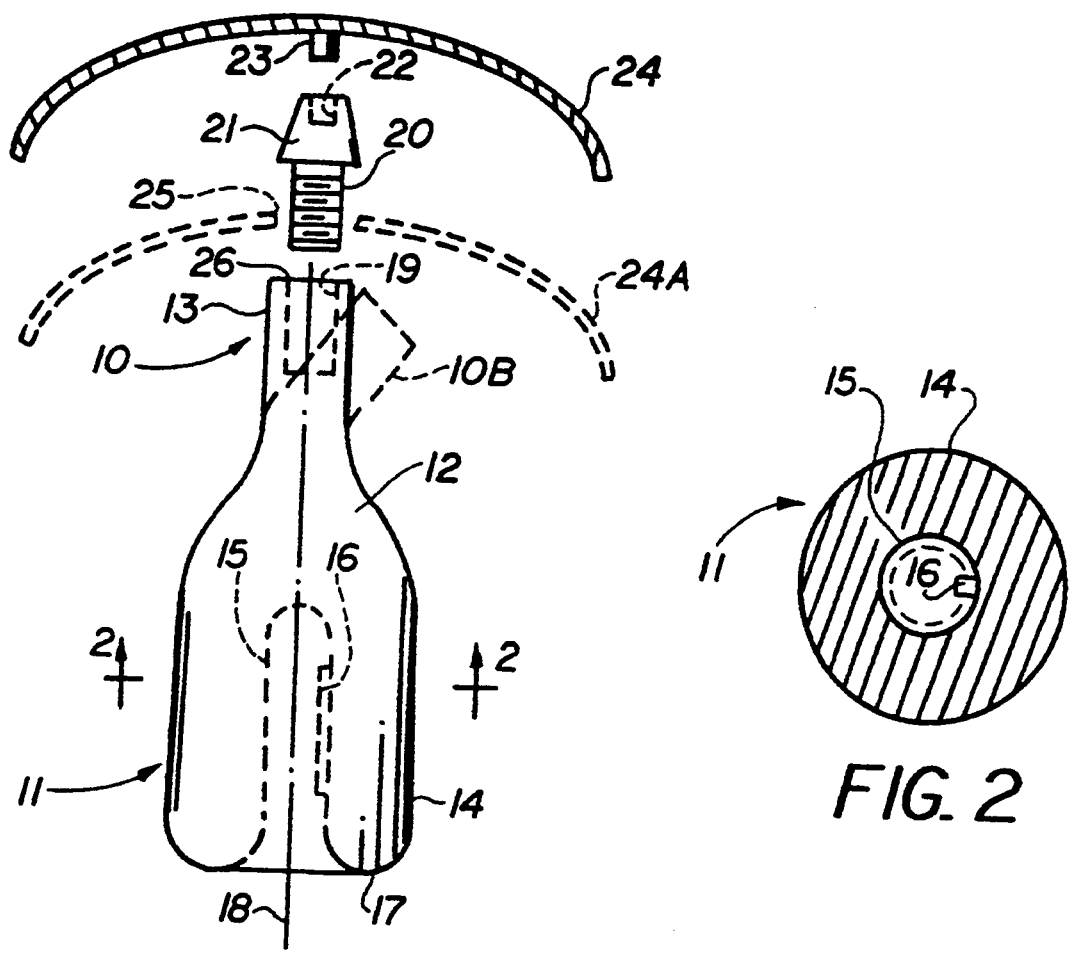
FIG. 1
FIG. 2
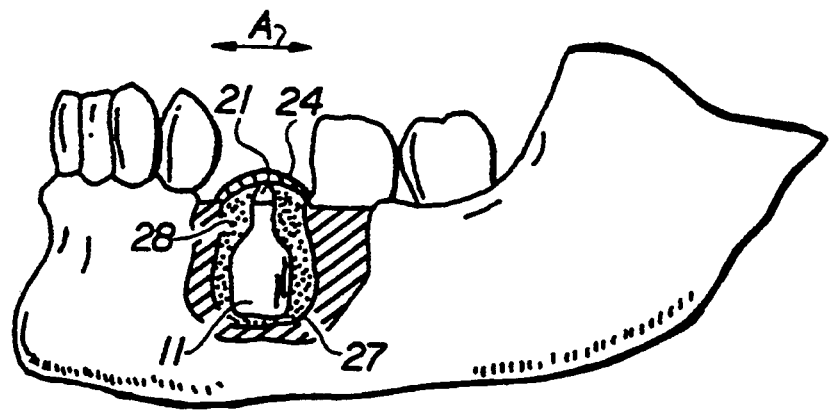
FIG. 3

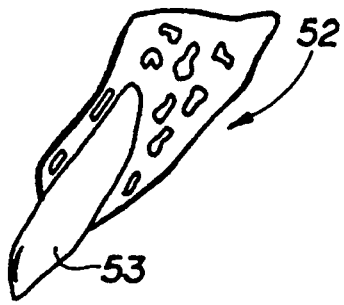
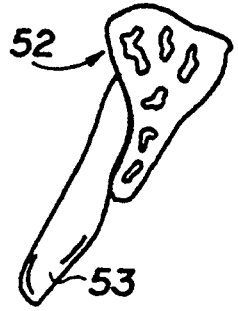
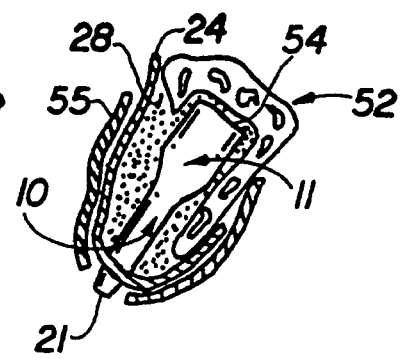
FIG. 10A  FIG. 10B  FIG. 10C
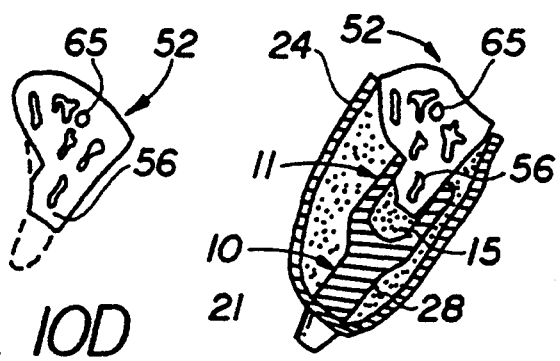
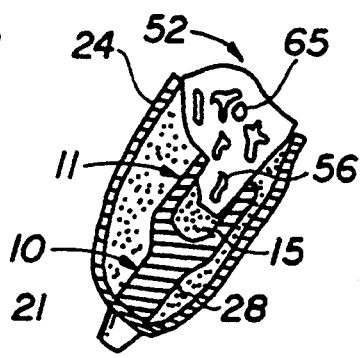
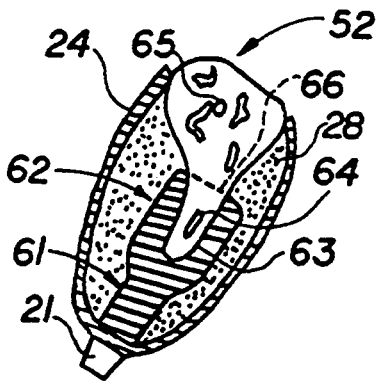
FIG. 10D  FIG. 10E  FIG. 10F

METHOD FOR INSTALLATION OF A DENTAL IMPLANT

This invention relates to a method and apparatus for installing a dental implant in the alveolar or basal bone of a patient.

More particularly, the invention relates to a method and apparatus for a dental implant which reduces the likelihood of the implant becoming infected, which does not require an opening of precise size to be drilled or formed in the alveolar bone to receive the dental implant, which can mount an implant on existing alveolar bone without requiring alteration of the structure of the bone, which prevents the juncture of the dental implant and artificial tooth attached to the implant from being exposed in the event the patient's gums recede, which enables bone mass lost as the patient ages to be replaced, and which enables an implant to be used when drilling an opening in the alveolar bone is precluded due to the existence of a nerve in the bone.

Dental implants are well known in the art. See, for example, U.S. Pat. Nos. 5,006,070 to Komatsu, 4,693,686 to Sendax, 4,812,120 to Flanagan et al., 4,818,559 to Hama et al., 4,671,768 to Ton, and 4,175,565 to Chiarenza et al. Such prior art dental implants and methods for installing the same have disadvantages.

First, the implants normally must be press fit or wedged into an opening formed in the alveolar bone. Force fitting an implant into the alveolar bone is not desirable because it is uncomfortable for the patient, runs the risk of cracking the jaw bone, further damages the bone, and, most importantly, increases the likelihood of infection because dental implants ordinarily are provided with an assortment of ridges, points, or teeth which serve as desirable sites for bacteria, both before and after the implant is inserted in the bone. As a consequence, dental implants typically appear medieval.

Second, force fitting an implant in the alveolar bone requires that the opening formed in the bone have a specific size which roughly conforms to the outer dimensions of the implant so the implant can be force fit into the opening. If a dental surgeon selects a drill of improper size, or waggles the drill while forming the hole in the alveolar bone, the implant may not seat properly in the bone and will work free from the jaw.

Third, the surface area of the portion of the implant imbedded in the jaw is typically reduced because of the common belief that fenestrations of various size must be formed in the implant to permit bone to grow through and anchor the implant.

Fourth, conventional implant procedures often can not be used because the drilling of a opening in the alveolar bone is prohibited by a nerve which passes through the bone.

Fifth, conventional implant procedures also often can not be successfully used when the jaw bone has significantly receded, as can be the case with older patients.

Sixth, conventional implant procedures do not offer a way of replacing alveolar bone which has been lost due to aging or to some other cause resulting in injury to the bone.

Seventh, conventional implant procedures typically do not permit the ready adjustment of the position of the implant after the implant is inserted in the opening formed in the alveolar bone. Correcting the position of an improperly installed implant is often difficult, unless the implant is completely removed from the alveolar bone, which is a time consuming process.

Accordingly, it would be highly desirable to provide an improved dental implant method and apparatus which would not require the force fitting of an implant in the alveolar bone, would not require the formation of a specific size opening in the jaw bone, would provide an implant less likely to loosen after being inserted in the alveolar bone, would permit an implant to be used on alveolar bone housing a nerve, would enable implants to be successfully utilized on alveolar bone which has receded with age, and would permit the position of the implant to be readily adjusted after the implant is inserted in an opening in the alveolar bone.

Therefore, it is a principal object of the invention to provide an improved dental implant method and apparatus.

Another object of the invention is to provide an improved dental implant which can be inserted in an opening in the alveolar bone without requiring that the opening must, within close tolerances, have a specific shape and dimension.

A further object of the invention is to provide an improved dental implant which permits ready adjustment of the position of the implant after the implant is placed in an opening formed in the jawbone.

Still another object of the invention is to provide a dental implant method which permits an implant to be attached to alveolar bone housing a nerve.

Yet a further object of the invention is to provide a dental implant method which allows an implant to be utilized on alveolar bone which has experienced significant loss and recession of its mass.

Another and further object of the instant invention is to provide an improved dental implant which is less likely to loosen after insertion in the alveolar bone.

These and other, further and more specific objects and advantages of the invention will be apparent to those skilled in the art from the following detailed description thereof, taken in conjunction with the drawings, in which:

FIG. 1 is a front view of a dental implant apparatus constructed in accordance with the principles of the invention;

FIG. 2 is a section view of the dental implant apparatus of FIG. 1 illustrating internal construction details thereof;

FIG. 3 is a side view of a portion of the lower jaw bone illustrating the implant of FIG. 1 installed in an opening formed in alveolar bone;

FIG. 10A is a side section view illustrating normal alveolar bone structure around an incisor tooth;

FIG. 10B is a side section view illustrating the recession of the alveolar bone structure from around the incisor tooth of FIG. 10A;

FIG. 10C is a side view illustrating the insertion of an implant in the bone structure of FIG. 10C after the incisor tooth is removed or falls out;

FIG. 10D is a side view illustrating the alveolar bone structure of FIG. 10B after the incisor tooth is removed and a circular drill is used to cut away some of the alveolar bone to form a cylindrical anchor peg;

FIG. 10E is a side partial section view illustrating a dental implant slidably installed on the anchor peg of FIG. 10D and packed with a malleable hydroxyapatite composition;

FIG. 10F is a side partial section view illustrating the alveolar bone structure of 10B after the incisor tooth is removed and an implant is slid onto the existing alveolar bone structure without altering the structure;

Figure 4:
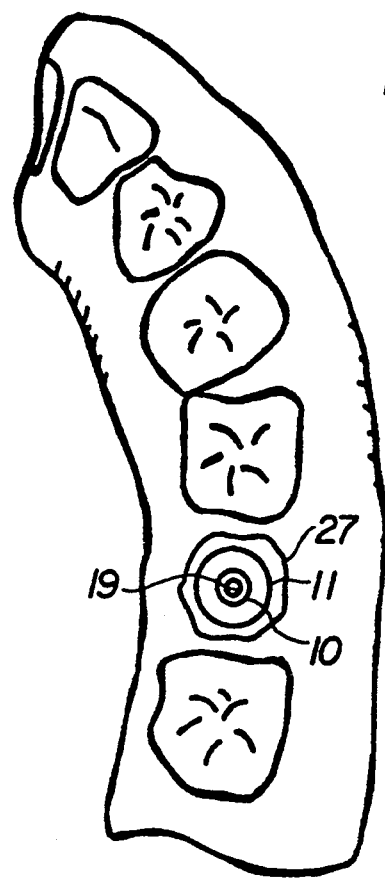
FIG. 4 is a top view of a portion of the jaw bone of FIG. 3 further illustrating the installation of the implant of FIG. 1 therein.
Figure 5:
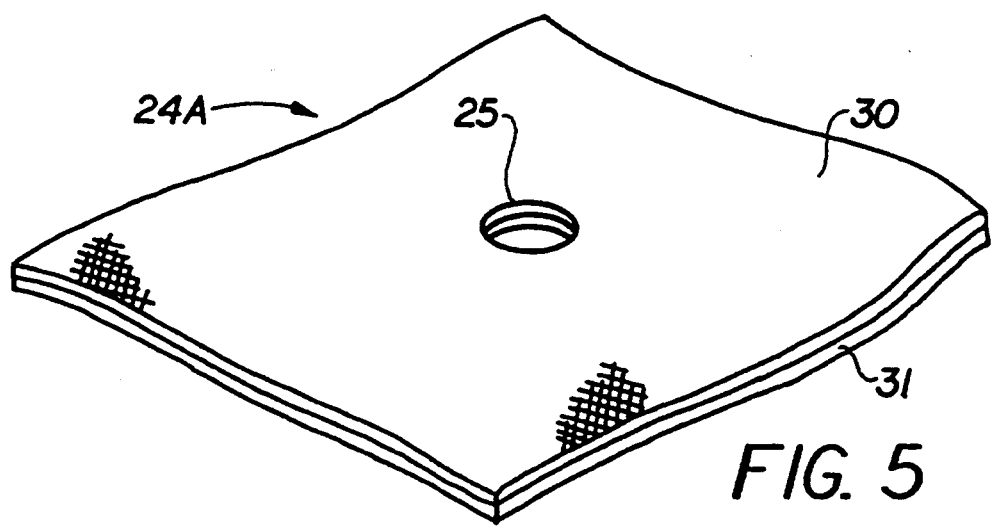
FIG. 5 is a perspective view illustrating a sheet of protective material used to shield hydroxyapatite composition used to pack an implant into an opening in the alveolar bone.

Briefly, in accordance with my invention, I provide an improved dental implant. The implant comprises a body having a closed top and a bottom and a longitudinal axis extending through the top and bottom; and, a head supported on the top of the body and adapted to support an artificial tooth. The body extends downwardly from the top and terminates at a lower end remote from the head. The body includes a smooth continuous surface extending from the top to the bottom and defining the periphery of the top and the bottom. The smooth surface circumscribes the longitudinal axis. The body also includes a hollow centrally defined therein, circumscribed by the continuous surface, and extending into the body through the bottom a selected distance toward the top. The hollow only opens at the lower end of the body. The head can have a smaller width than the body. The hollow can be an involute. The continuous surface can be shaped such that when any cross section of the body is taken perpendicular to the longitudinal axis, each point on the continuous surface is generally equidistant from the longitudinal axis.

In another embodiment of the invention, I provide a method of anchoring a dental implant in the alveolar bone of a patient. The method comprises the steps of forming an opening in the alveolar bone; inserting a dental implant in the opening, the implant comprising a body and a head supported on the body and adapted to support an artificial tooth, the dental implant only partially filling the space in the opening; and, packing the space in the opening which is unoccupied by the dental implant with a hydroxyapatite composition. The opening can be large enough to permit the implant to be readily tilted from side to side after insertion in the opening. After the opening is packed with hydroxyapatite composition, the implant can be adjusted or tilted from side to side and the hydroxyapatite composition then repacked.

In a further embodiment of the invention, I provide a dental implant comprising a body; a head supported on the body and having a longitudinal axis and including an upper portion adapted to support an artificial tooth and having a distal tip and a peripheral surface circumscribing the longitudinal axis and extending downwardly from the distal tip toward the body, and, a lower portion supported on the body; and, a healing cap. The healing cap is adapted to be removably attached to the upper portion of the head and includes a prophylactic portion which, when the healing cap is attached to the upper portion, slidably extends downwardly from the tip over and covers at least a portion of the peripheral surface such that when the implant is inserted in an opening in the alveolar bone, a solidified filler composition at least partially fills the opening, extends downwardly from the distal tip toward the body, and covers the prophylactic portion, the lower portion, and the body, and the healing cap is removed from the head, a space exists intermediate the portion of the peripheral surface and the solidified filler composition such that an artificial tooth can extend into the space and cover the distal tip of the head. The filler composition can be a hydroxyapatite composition.

In still another embodiment of the invention, I provide a method of anchoring a dental implant to the alveolar bone of a patient. The method comprises the steps of placing the dental implant at a selected site on the alveolar bone, the dental implant comprising a body and a head supported on the body and adapted to support an artificial tooth; packing a malleable hydroxyapatite composition around the dental implant and against alveolar bone of the patient; and, covering the malleable hydroxyapatite composition with a pliable sheet of material to at least partially prevent gum tissue from growing into the hydroxyapatite composition while the hydroxyapatite composition solidifies.

In yet another embodiment of the invention, I provide a dental implant for a ridge of alveolar bone normally at least partially covered by gum tissue. The implant comprises a body having a top and a pair of opposed feet each extending downwardly from the top to a tip at a lower end remote from the top, the feet having an inner surface shaped, contoured, and dimensioned to conform to the ridge of alveolar bone when the gum tissue is removed from the ridge; and, a head supported on the body and adapted to support an artificial tooth.

In yet still another embodiment of the invention, I provide a method of anchoring a dental implant to the existing alveolar bone of a patient, the bone having an existing outer surface. The method comprises the steps of removing alveolar bone to form an outwardly projecting anchor peg having a selected shape and dimension; and, inserting a dental implant over the anchor peg. The dental implant comprises a body and a head support on the body and adapted to support an artificial tooth. The body extends downwardly from the head to a lower end remote from the head and having an aperture formed in the lower end. The aperture is shaped and dimensioned to be slidably inserted on and conform to the outwardly projecting anchor.

Turning now to the drawings, which depict the presently preferred embodiments of the invention for the purpose of illustrating the practice thereof and not by way of limitation of the scope of the invention and in which like reference characters refer to corresponding elements throughout the several views, FIG. 1 illustrates dental implant apparatus which is constructed in accordance with the principles of the invention and includes a dental implant which has the general shape of a wine bottle and includes a cylindrical head 10 attached to a body 11. The closed top 12 of body 11 has a smooth continuous conical outer surface which tapers from the smooth continuous outer cylindrical surface 14 of the bottom 11 into the smooth cylindrical outer surface 13 of head 10. The conical outer surface of top 12, as do smooth cylindrical surfaces 14 and 13, completely circumscribes longitudinal axis and centerline 18. Head 10 can, if desired, be bent at some selected angle with respect to axis 18 and body 11 as indicated by dashed lines 10B or can be tapered in the manner of head 10A in FIG. 12. The bottom of body 11 extends downwardly from the top 12 and terminates at lower end 17 remote from the head 10. Involute or hollow 15 is formed centrally within body 11, is circumscribed by continuous surface 14, and extends upwardly into body 11 a selected distance toward top 12. Hollow 15 opens only at the lower end 17. Head 13 has a smaller diameter than body 11. An internally threaded aperture 19 is formed in head 13 to receive the externally threaded end 20 of a healing cap. The frustroconical head 21 of the healing cap has a cylindrical aperture 22 formed therein. Cylindrical member 23 is attached to pliable fabric sheet 24 and is shaped to be removably snap fit into aperture 22. The sheet 24 can be secured to the healing cap or head 10 using any convenient means. For example, an aperture 25 can be formed through a pliable sheet 24A and sized such that end 20 slides through aperture 25 and permits sheet 24A to be compressed between head 21 and the circular distal end 26 of head 10. Rib 16 outwardly depends from the smooth cylindrical wall circumscribing and defining hollow 15 and, when hollow 15 is filled with hydroxyapatite or bone in a manner which will be described, prevents the dental implant from rotating about axis 18. Most infection in a tooth begins at the gum line and works its way downwardly toward the root of the tooth. The smooth continuous outer surfaces 13, 14 of the implant of FIG. 1 facilitate determining how far, if at all, infection has penetrated downwardly along the outer surfaces of the implant. The extension of the outer surfaces of the implant from the distal end 26 of the head to the lower end 17 make it difficult for infection to enter hollow 15. In many conventional implants, once infection extends a short distance into the bone, it is a simple matter for the infection to spread laterally under portions of the implant. Consequently, in the implant of FIG. 1 it is important that perforations are not formed through the continuous outer surfaces 13, 14, or the conical surface of top 12. The large area of surfaces 13 and 14 and of the outer conical surface of top 12 help distribute the forces which are produced on an artificial tooth mounted on the implant and decrease the likelihood that the implant will come loose. The smooth curvature and lack of ridges or points extending outwardly from implant surfaces 13 and 14 also decreases the likelihood that stress fractures will be formed in the alveolar bone during the use of an artificial tooth attached to the implant.

The installation of the implant apparatus of FIGS. 1 and 2 in alveolar bone is illustrated in FIGS. 3 and 4. As shown in FIG. 4, an opening 27 is drilled or otherwise formed at a selected location in the alveolar bone and the dental implant is inserted in opening 27. FIG. 4 illustrates opening 27 immediately after the dental implant has been inserted therein. Opening 27 is larger than the dental implant so that the head 10 can be grasped manually or with a dental instrument and tilted from side to side in opening 27. The space between the dental implant and the sides of opening 27 which circumscribe the implant is packed with a malleable hydroxyapatite composition 28. Hollow 15 can also be packed with the hydroxyapatite composition 28 before the implant is inserted in opening 27. After the composition 28 is packed into opening 27 around the dental implant, the head 10 can, if desired, be laterally moved in directions like those indicated by arrows A to tilt and reposition the implant in opening 27. After the dental implant is in the desired position in opening 27, the hydroxyapatite composition is repacked, and member 23 is snapped into aperture 22 in head 21 to position sheet 24 over opening 27 in the manner illustrated in FIG. 3. Sheet 24 can be trimmed as appropriate to cover opening 27. Although not shown in FIG. 4, gum tissue ordinarily at least partially covers and helps maintain sheet 24 in its desired position. Sheet 24 can comprise GORTEX or any other suitable pliable material which helps prevent gum tissue from growing into the hydroxyapatite composition while it solidifies. If desired, sheet 24 can comprise a resorbable material. The GORTEX is left in place for a period of two to twelve months while the surrounding bone grows into and causes the hydroxyapatite composition to solidify and anchor the dental implant in place. After the hydroxyapatite composition has solidified, the healing cap and the sheet 24 are removed such that the gum tissue covers the solidified hydroxyapatite composition. The internally threaded aperture 19 in the head 10 of the implant is used to attach an artificial tooth to the implant.

GORTEX is produced by W. L Gore & Assoc., Inc. Regenerative Technologies of 3773 Kaspar Avenue, Flagstaff, Ariz. 86003-2500, USA. If desired, a pliable sheet 24A can include a layer of GORTEX or similar pliable material laminated with an undercoating of collagen, polyglycolic acid, or another desired material. The collagen imparts a stiffness to sheet 24A and over time is gradually dissolved by the body. GORTEX is an expanded polytetrafluroethylene (e-PTFE) material.

Hydroxyapatite is a crystalline substance containing calcium and phosphorus and is found in certain rocks. It is the basic constituent of bone. The hydroxyapatite composition used to pack opening 27 can simply comprise a dry hydroxyapatite powder. The hydroxyapatite is, however, normally mixed with a liquid substance to form a slurry or more malleable composition which is more readily packed and remains in fixed position than dry hydroxyapatite powder. Hydroxyapatite powder can be mixed with water, plaster, collagen, dextran, epinephrine, or some other desirable material. The hydroxyapatite can be obtained from natural mineral sources, from ground bone, etc. Materials other than hydroxyapatite compositions can be used to fill and pack opening 27. Such other materials can include organic and inorganic matrices and/or combinations thereof. These matrices can be porous, non-porous, active and/or resorbable matrices, or totally inert. For example, coral and coral analogs, polymethyl methacrylate, polyethylene, PTFE (polytetrafluroethylene), polysufone, polymers, polyethylene glycols, osteomin (bone ash), autogenous bone, freeze dried demineralized bone, resorbable and non-resorbable hydroxyapatite, xenographs (bovine), miniscrews, allografts, composites, polyethylene glycol propionaldehyde, HAPSET, or the patient's own bone can be utilized.

Figure 6:
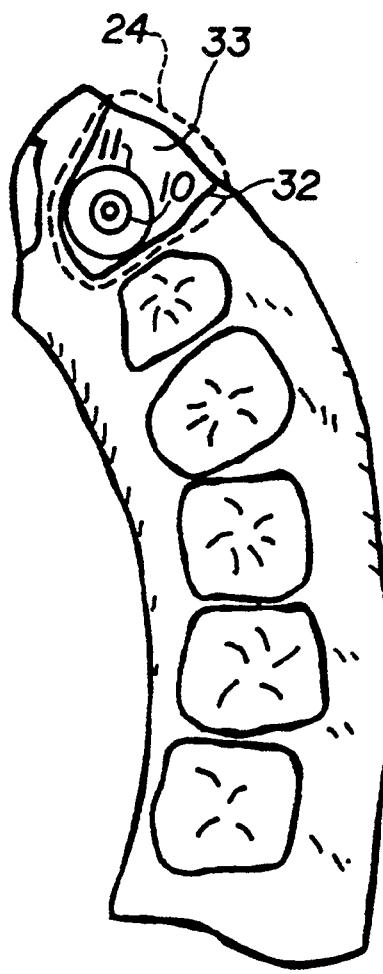
FIG. 6 is a top view of a portion of the lower jaw bone illustrating the insertion of an implant in an opening formed by laterally drilling into the jaw bone.
Figure 7:
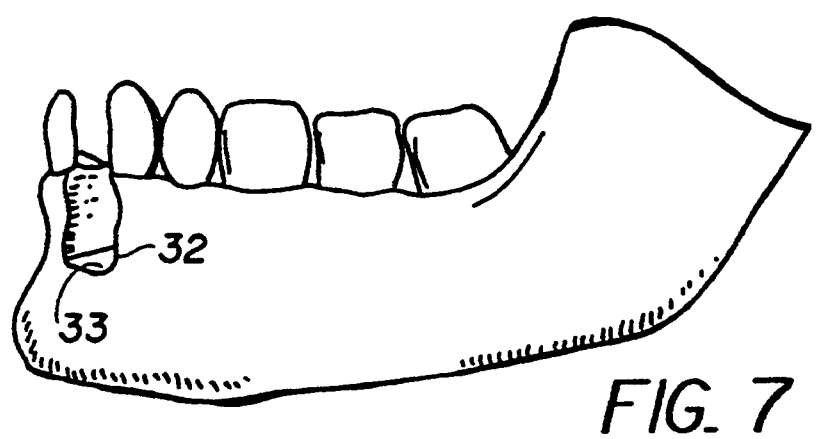
FIG. 7 is a side view of the jaw bone of FIG. 6 further illustrating the lateral opening formed in the jaw bone.

In some cases, it is preferable to produce an opening for a dental implant by forming an aperture in the alveolar bone which opens laterally or outwardly away from the inside of the patient's mouth. Such an outwardly opening aperture 32 is illustrated in FIGS. 6 and 7. In FIG. 7, the dental implant has not yet been inserted on floor 33 of aperture 32. FIG. 6 illustrates the implant in aperture 32. A malleable hydroxyapatite composition is utilized to pack the dental implant in aperture 32. Once aperture 32 is packed with hydroxyapatite composition and the implant is properly positioned in the hydroxyapatite composition and aperture 32, a healing cap is used to attach a pliable layer 24 of material to head 10 to protect the hydroxyapatite composition from invasion by epithelial or other living tissue while the composition hardens. After an appropriate period of time has passed and the bone has grown into and hardened the hydroxyapatite composition, the healing cap and layer of material are removed and an artificial tooth is attached to head 10 using internally threaded aperture 19.

Figure 8:
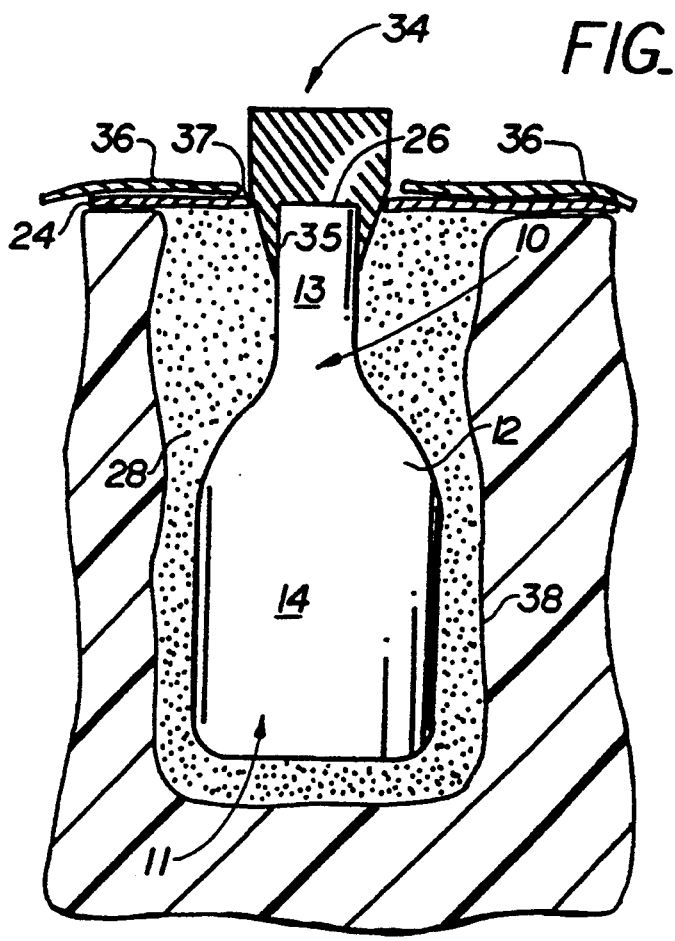
FIG. 8 is a side partial section view illustrating an alternate embodiment of the implant of the invention inserted in an opening formed in the alveolar bone.
Figure 8A:
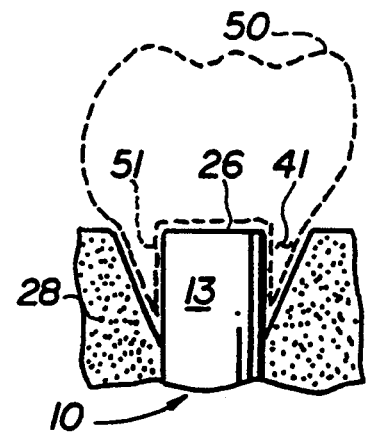
FIG. 8A is a side view illustrating a portion of the implant of FIG. 8 after the healing cap is removed.
Figure 9:
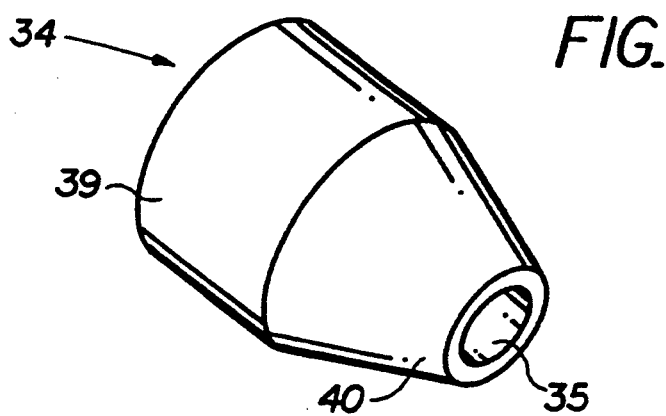
FIG. 9 is a perspective view illustrating a healing cap used in the implant of FIG. 8.

An alternate embodiment of a healing cap 34 is illustrated in FIGS. 8 and 9. Cap 34 includes internal cylindrical aperture 35 shaped to slidably fit over the circular distal end 26 of head 10 and to cover at least a portion of the cylindrical peripheral surface 13 of head 10 of the wine bottle shaped implant of FIG. 1. The pliable sheet 24 in FIG. 8 has a circular aperture 37 formed therethrough which is large enough to slide a selected distance up the conical tip of cap 34, in the manner shown in FIG. 8, but which is too small to slide over the cylindrical upper end 39 of cap 34. Consequently, the conical end 40 of cap 34 functions to hold the sheet 24 in position against the hydroxyapatite composition 28 in the manner illustrated in FIG. 8. Further, a portion of the conical end 40 of cap 34 extends downwardly along surface 13 and past end 26 so that after the composition 28 has solidified and cap 34 is removed from head 10, a conically shaped space 41 (FIG. 8A) exists intermediate the solidified composition 28 and the upper portion of surface 13. When an artificial tooth 50 is subsequently attached to head 10 using the internally threaded aperture 19 formed therein, the lower portion of tooth 50 can include a cylindrical aperture 51 which slides over the upper end of head 10 and covers distal end 26. As would be appreciated by those of skill in the art, either sample implants or impression analogs of the head 10, 10A (FIG. 12) of the support member 70 (FIG. 12) of each implant can be provided to a dental laboratory so that the lower margins of an artificial tooth 50 can be perfectly sized to extend into and completely fill the conically shaped space 41. Distal end 26 ordinarily is positioned at the gum line after the implant is inserted in an opening 38 formed in the alveolar bone. Accordingly, the portions of the artificial tooth 50 extending into space 41 extend below the gum line of the patient.

FIG. 10A illustrates a normal, healthy alveolar bone 52 supporting an incisor tooth 53. In FIG. 10B, the bone 52 has receded due to age or other factors. In Fig. 10C, tooth 53 has been removed; a cylindrical aperture 54 has been drilled or otherwise formed in the bone 52; an implant has been inserted in aperture 54; a malleable hydroxyapatite composition 28 has been packed into aperture 54, around the implant, and against the bone 52; a layer of pliable material 24 has been attached to head 10 with the head 21 of a healing cap and extends over the hydroxyapatite composition 28; and, the gum tissue has been positioned over material 24. After the bone 52 grows into the hydroxyapatite composition 28 and the composition 28 solidifies, the healing cap and material 24 are removed, and an artificial tooth is attached to head 10. The hydroxyapatite composition applied to the implant and bone 52 in FIG. 10C is used to augment or build the bone 52 back up to a shape and dimension resembling or duplicating its original normal shape and dimension illustrated in FIG. 10A. A particular advantage of the dental implant methodology of the invention is that it permits hydroxyapatite compositions to be used to augment and enlarge existing alveolar bone structure while at the same time facilitating the anchoring of an implant to alveolar bone. To facilitate the anchoring of an implant in the existing alveolar or basal bone, indents or grooves can be formed in the bone or in the surface of the implant to receive hydroxyapatite or other material used to fill or pack into or around the alveolar or basal bone and the implant.

In FIG. 10D, the tooth 53 has been removed from the alveolar bone 52 of FIG. 10B and a circular drill has been used to remove some of the bone 52 to form a cylindrical anchor peg 56 which is shaped and dimensioned to be slidably received by the involute 15 of the implant of FIG. 1 in the manner illustrated in FIG. 10E. After involute or hollow 15 is slid onto peg 56, malleable hydroxyapatite composition is packed around the body 11 and head 10 of the implant and the head 21 of the healing cap is used to attach pliable material 24 to head 10. If desired, hydroxyapatite composition 28 can also be inserted in hollow 15 before hollow 15 is slid onto peg 56. One the hydroxyapatite composition has solidified, the healing cap and material 21 are removed, and an artificial tooth is attached to head 10. The bone 52 illustrated in FIGS. 10D and 10E includes a nerve 65.

Figure 11:
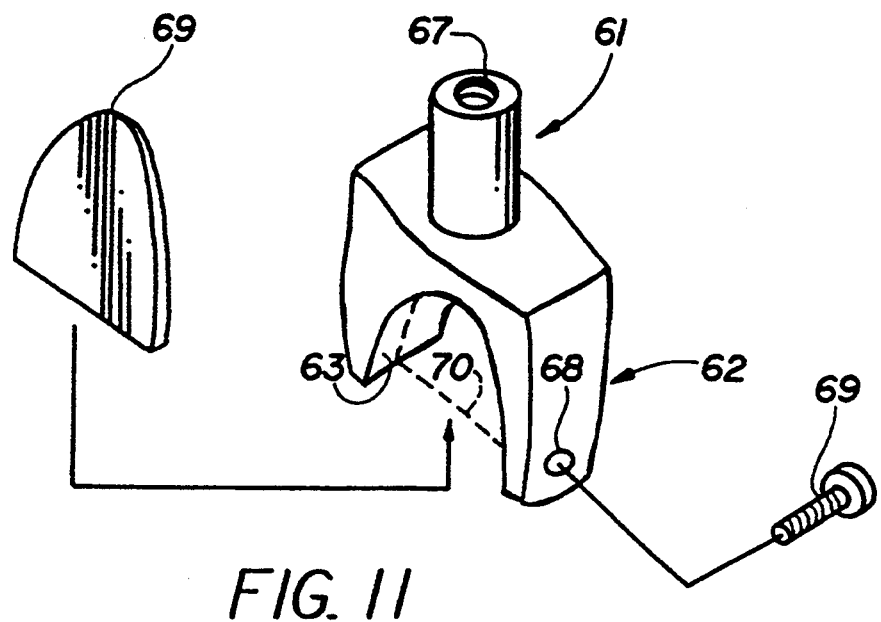
FIG. 11 is a perspective view illustrating an implant of the type which can be fit to an existing alveolar bone structure.

In FIG. 10F, the tooth 53 has been removed from the alveolar bone 52 of FIG. 10B and shape of the ridge 64 of bone 52 has not been altered. An implant has been placed on ridge 64. The implant includes head 61, body 62, and arch or U-shaped aperture 63. Aperture 63 is shaped and dimensioned to conform to and slide on to ridge 64 in the manner illustrated in FIG. 10F. The implant of FIG. 10F can be formed by making a mold of ridge 64 and using the mold to eventually produce an implant with an aperture 63 which will conform to ridge 64. Various techniques for making a mold of ridge 64 and using the mold to produce a duplicate of the ridge or to produce a shape which will conform to the ridge 64 are well known in the art and will not be discussed herein. After the implant of FIGS. 10F and 11 is slidably inserted on ridge 64 in the manner shown in FIG. 10F, malleable hydroxyapatite composition is pressed against and molded around against the implant and bone 52 and covered with a layer 24 which is secured to head 61 by head 21 of the healing cap illustrated in FIG. 1. The externally threaded end 20 of the healing cap is rotated into internally threaded aperture 67 formed in the upper end of head 61. If desired, an aperture(s) 68 can be formed through body 62 to permit a screw(s) to pass through the aperture 68 and into the bone 52 to secure the implant to the bone 52. In addition, a slot, indicated by dashed lines 66 in FIG. 10F, can be cut through ridge 64 to receive a panel 69 which is attached to arch 63 in the position indicated by dashed line 70.

Figure 12:
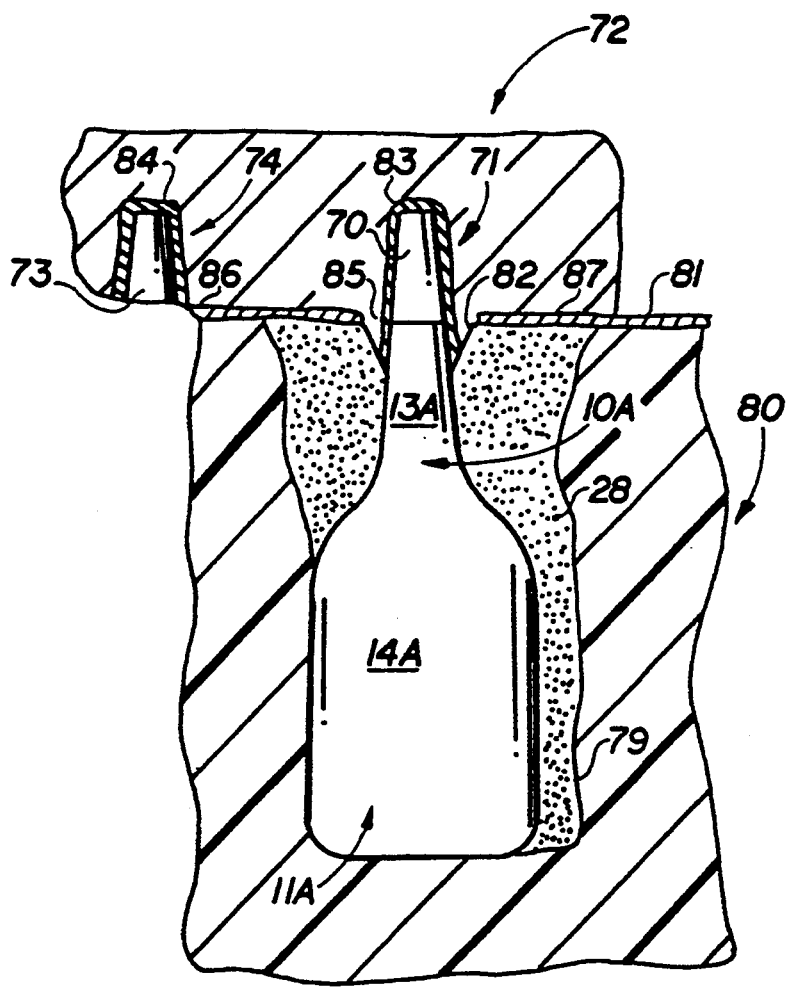
FIG. 12 is a side partial section view illustrating a molding procedure utilized in another embodiment of the invention.
Figure 13:
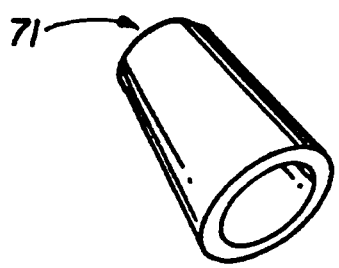
FIG. 13 is a perspective view of a sacrificial coping utilized in the embodiment of the invention illustrated in FIG. 12.

FIGS. 12 to 15 depict apparatus using in a molding method which is used in conjunction with the implant apparatus and methodology of the invention. In FIG. 12, an implant having a head 10A and bottom 11A is held in position in opening 79 formed in alveolar bone by a solidified hydroxyapatite composition 28. Composition 28 solidified when the surrounding alveolar bone 80 grew into the composition 28 in opening 79. Head 10A has a conical head which tapers upwardly from body 11A toward the gum tissue 81. Head 10A has outer smooth continuous surface 13A. Body 11A includes outer smooth continuous surface 14A. Frustoconical support member 70 is attached to head 10A. Sacrificial frustoconical coping 71 is slid over member 70. Sacrificial frustoconical coping 74 is slid over member 73. If desired, copings 71 and 74 can be metal and not be sacrificial. Member 73 is attached to the head 10A (not shown) of another implant (not shown) in the alveolar bone 80. Rubber, silicone, or some other acceptable material is used to form a negative mold 72 extending over and around copings 71 and 74 in the manner shown in FIG. 12. The use of such molding materials in dentistry is well known and will not be discussed herein. The negative mold includes upstanding hollow conical member 85; frustoconical hollows 83 and 84 which conform and adhere to copings 71 and 74, respectively; and, surfaces 86 and 87 which conform to gum tissue 81. When the negative mold 72 is removed from members 70 and 73, copings 71 and 74 are removed with and are imbedded in the mold 72.

Figure 14:
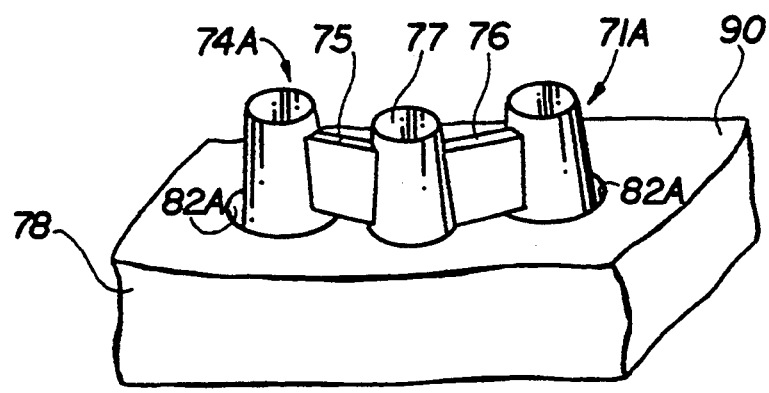
FIG. 14 is a perspective view illustrating another step in the molding procedure of FIG. 12.
Figure 15:
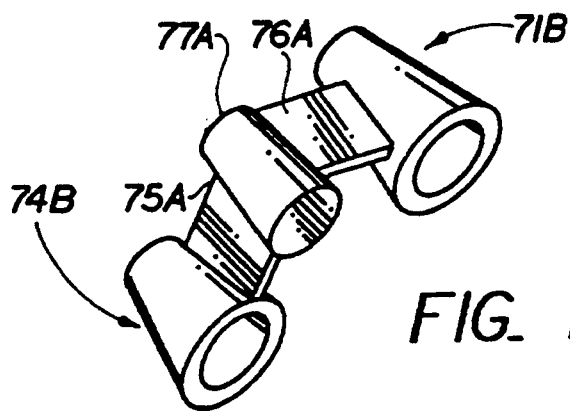
FIG. 15 is a perspective view illustrating a finished dental bridge produced according to the method of FIGS. 12 and 14.

After mold 72 has set and is removed from members 70 and 73 and from the patient's mouth, mold 72 is used to make a positive stone mold 78. This is, as is well known, accomplished by inverting mold 72, place mold 72 in a container which circumscribes mold 72, and by pouring a stone mold slurry into sacrificial copings 71 and 74 and over surfaces 86 and 87. After the stone mold slurry hardens to form mold 78, the mold 78 and mold 72 are heated until mold 72 melts and flows off of stone mold 78, or, mold 72 can simply be peeled off of the hardened stone mold with or without copings 71 and 74. The positive stone mold 78 which remains replicates the gum line 81, support members 72 and 73, and the upper portion of each head 10A as shown in FIG. 12. The stone mold 78 also replicates 82A the conical groove or detent 82 formed around the upper portion of each implant head 10A. In FIG. 14, each conical groove 82 has a shape and dimension equal to the shape and dimension of conical groove 82 in FIG. 14. Also, in FIG. 14, the portions of the stone mold which replicate frustoconical members 70 and 73 are not visible because new sacrificial copings 71A and 74A have been slipped over said portions of the stone mold (or the copings 71 and 74 which were originally used in the mouth to make mold 72 can remain on said portions of the stone mold). While the shape and dimension of each coping can vary, in FIGS. 12 to 14, each coping 71, 74, 71A, 74A is of equivalent shape and dimension. The shape and dimension of each support member 70 and 73 can also vary as desired. In FIG. 12, however, each frustoconical support member 70 and 73 is of equal shape and dimension.

In FIG. 14 a pontic comprised of frustoconical support member 77 and ribs 75 and 76 has been constructed above the upper surface 90 of stone mold 78. The pontic interconnects sacrificial copings 71A and 74A and is positioned adjacent surface 90. The pontic is typically constructed from wax, but any other desired material can be utilized. Once the construction of the pontic is completed, the sacrificial bridge support of FIG. 14 is removed from mold 78 and mold 78 is discarded, or, mold 78 is retained for use in subsequent porcelain work. After the sacrificial bridge support is removed from mold 78, its shape and dimension and appearance is identical to that of the finished metal bridge support pictured in FIG. 15.

In the next step of the molding process, the sacrificial bridge support is submersed or "invested" in a stone mold slurry and, before or as the slurry hardens, a small escape channel is formed which leads from the sacrificial bridge support through and to the upper surface of the slurry. After the stone mold slurry hardens, it is heated to melt the wax pontic and the sacrificial copings 71A and 74A. The melted wax and melted materials from the copings 71A and 74A flows out of the stone mold through the escape channel. After all of the melted material flows out of the stone mold, a hollow exists in the stone mold which is a negative of the sacrificial support bridge of FIG. 14 and of the bridge of FIG. 15. The investment molding process is continued by pouring molten metal through the escape channel into this hollow and allowing the metal to harden. After the metal hardens, the finished support bridge of FIG. 15 has been formed in the stone mold. The stone mold is broken away from the bridge to free the finished bridge from the mold. Porcelain or another desired material is placed on the bridge supports 74B, 77A, and 71B to build artificial teeth on the bridge. Ordinarily, a single artificial tooth is built on each bridge support. After artificial teeth are constructed on the bridge supports, the bridge is inserted in the patient's mouth by placing hollow support 71B over member 70 and by placing hollow support 74B over member 73. Supports 74B and 71B can be glued or otherwise affixed to members 73 and 70, respectively.

Figure 16:
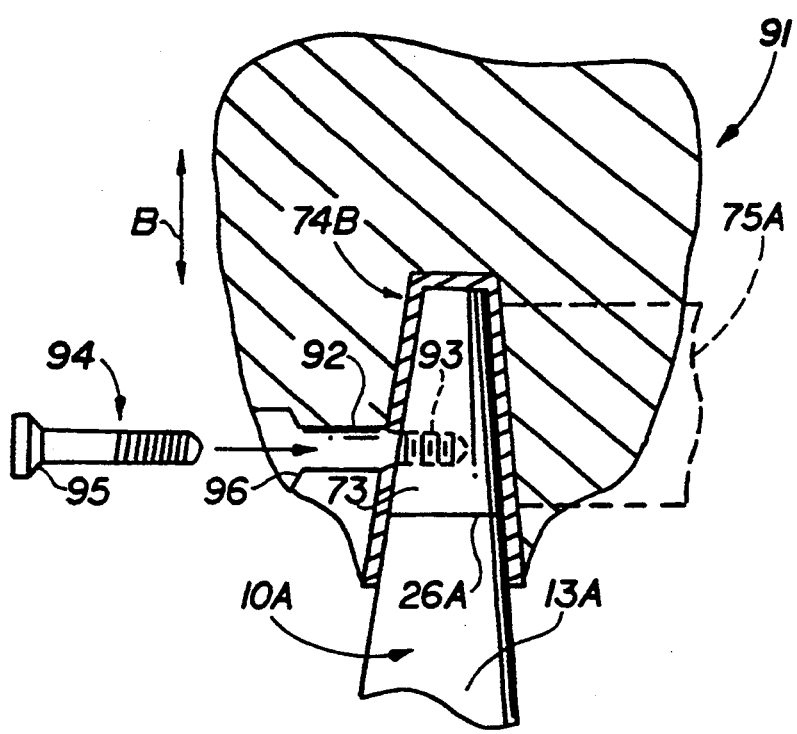
FIG. 16 is a side partial section view illustrating an artificial tooth removably attached to an implant apparatus.

A method of removably attaching a bridge support 74B and artificial tooth 91 to a member 73 is illustrated in FIG. 16. In FIG. 16 a fastener 94 is inserted into aperture 92 and threaded into internally threaded aperture 93 in member 73. Precise alignment of apertures 92 and 93 is not required because the diameter of aperture 92 is slightly larger than that of aperture 93. The undersurface 95 of fastener conforms to and bears against a portion of conical surface 96 to prevent the tooth 91 from moving in the directions of arrows B. When fastener 94 is removed from apertures 92 and 93, coping 74B can be pulled upwardly off of and free from support member 73.

In FIG. 16, the upper distal end 26A of head 10A contacts the bottom of support member 73. The outer peripheral conical surface of head 10A is contiguous with and lies in a common conical plane with the outer conical surface 13A of head 10A. Coping 74B conforms to surface 13A and to the outer conical surface of member 73 so that coping 74B slidably engages and fits said conical surfaces in the manner illustrated in FIG. 16. The co-planar relationship of the conical surface of member 73 and the conical surface 13A of member 10A is important in the practice of the invention because it enables coping 74B and tooth 91 to extend sealingly downwardly below the gum line, i.e. to extend downwardly below end 26A.

Members 70 and 73 can be fabricated from metal or from plastic, rubber, copolymer, polymer, composites, or any other desired material, as can the sacrificial copings 71, 74, 71A, 74A.

The implant method and apparatus of the invention have several advantages. First, since the opening which is formed in the bone to receive the implant does not have to conform to the shape and dimension of the implant, special drills are not necessary when the opening is formed in the alveolar or basal bone to receive the implant. Second, drilling an opening in the bone which is larger than and does not conform to the shape and contour of the implant decreases the amount of heat generated during the drilling process. This is important because bone is damaged when exposed to heat in excess of 130 degrees centigrade for one minute or more. Conventional implants require that a cylindrical opening be drilled in the bone. Drilling such openings requires the use of internally irrigated slowly rotating burrs and is more likely to generate heat which damages the bone adjacent the cylindrical opening. When an opening is drilled for the implant of the invention, a higher speed externally irrigated burr can be utilized. Third, the implant of the invention permits non-resorbable hydroxyapatite to be utilized to fill in the opening around the implant. The non-resorbable hydroxyapatite produces a strong, tough structure which is less likely to have saucerization. Saucerization occurs when bone is lost from around the implant due to stress or bacterial invasion. This use of non-resorbable hydroxyapatite is particularly advantageous when a bone ridge which has receded is being augmented to duplicate the original shape and size of the ridge. Fourth, the lateral insertion of an implant in the manner illustrated in FIGS. 6 and 7 is useful in the case where a tooth has been missing for some time and adjacent teeth have migrated into and partially filled the space of the missing tooth. When this occurs, conventional implants either are forced to be so small that they are weak or are prevented from being utilized due to the small size of the space remaining between the adjacent teeth. The implant of FIGS. 1 and 8 solves this problem because it has a large base with a thin neck which can extend between the remaining adjacent teeth. Fifth, the implant method of the invention covers the junction between a support member 70 and the head 10A (FIG. 12) of the implant. In conventional implants, this junction is exposed to oral fluids and can corrode and fail. Further, dentists often do not screw or otherwise install member 70 snugly against the top of head 10A, leaving a septic gap. Sixth, the implant of FIGS. 1, 8 and 12 can be long or short and still provide a large outer surface area for anchoring the implant in the alveolar or basal bone.

Figure 17:
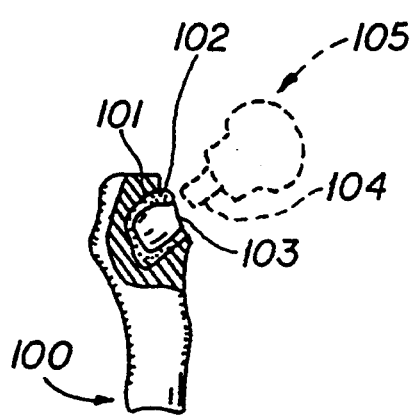
FIG. 17 is a side partial section view illustrating a hip implant procedure; and, FIG. 18 is a partial side section view illustrating an interlocking opening formed in bone during an implant procedure according to the invention.

As would be appreciated by those of skill in the art, the implant methodology described above in connection with dental implants can be utilized to carry out implants in bone throughout the body. For example, in FIG. 17, the "ball" at the top of femur 100 has been removed and an oversized opening 101 has been formed in the top of femur 100. Implant 103 is inserted in opening 101. The lower portion of implant 103 is the body thereof and the upper portion of implant 103 (the portion nearest artificial "ball" 105) is the head of the implant 103. Each implant in the prior art and illustrated herein includes a lower portion, or body, and an upper portion, or head. A hydroxyapatite (HA), hydroxyapatite cement (HAC) or other composition 102 is packed around implant 103 to secure implant 103 in opening 101. An internally threaded cylindrical aperture (not visible) is formed in implant 103 to receive the externally threaded end 104 of an artificial "ball" 105. It is advantageous to form opening 101 by laterally cutting or drilling into the top of femur 100 in the manner illustrated in FIG. 6. This reduces the amount by which the femur has to be laterally displaced away from the hip socket during formation of opening 10, thus reducing trauma to surrounding nerves, muscles, blood vessels and soft tissue.

Figure 18:
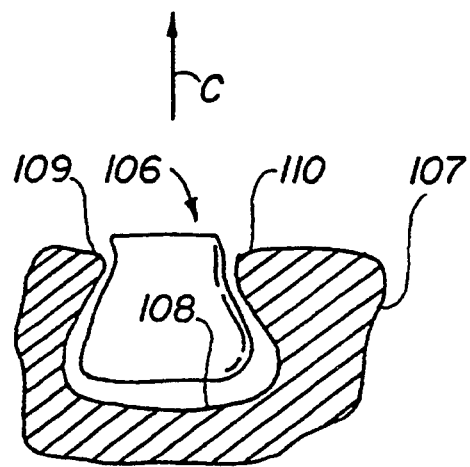

In FIG. 18, the opening 108 in bone 107 and the implant 106 are shaped and dimensioned such that when implant 106 is laterally slid into opening 108, a mechanical lock is formed and implant 106 cannot be removed from opening 108 in the direction of arrow C. Similarly, opening 108 and implant 106 can be formed such that implant 106 is inserted in opening 108 in the direction directly opposite that of arrow C and is rotated 90 degrees about an axis parallel to arrow C such that after implant 106 is so rotated, it cannot be displaced out of opening 108 in the direction of arrow C because the longer dimension of implant 106 has been turned to a position similar to that shown in FIG. 18 under the inwardly extending lips 109 and 110 of opening 108.

The opening 108 illustrated in FIG. 18 can be formed and an implant inserted in opening 108 which flares outwardly like implant 106 but which can be readily withdrawn from opening 18 in the direction of arrow C. The implant is anchored in opening 108 by packing HA, HAC, or another composition in opening 108 and around implant 106.

The composition 102 used to pack around an implant 103 can include magnetic fibers and have a viscosity which permits the fibers to align when a magnetic force is applied to the composition. The composition 102 can also, in combination with the magnetic fibers or in place of the magnetic fibers, include fibers which do not respond to the magnetic force.

As noted earlier, active compositions can be utilized in combination with or in place of hydroxyapatite compositions. Such active compositions, or tissue growth factors, can be intermixed with hydroxyapatite or other materials utilized as packing around an implant, can be coated on an implant 103, or can be inserted in situ intermediate the implant 103 and opening 101 to cause, for example, the bone to grow back inwardly toward the implant. In the event implant 103 is coated with a bone growth factor or a bone growth factor is inserted in situ intermediate an implant 103 and opening 101 in the bone, positioning means can be utilized to maintain implant 103 in its desired position in opening 101 until bone ingrowth contacts implant 103 and maintains it in position. The positioning means can also be utilized to maintain an implant in position until a filler material is packed in opening 101 around the implant to anchor the implant in position. Such positioning means can consist of a collar or template which fixedly and/or resorbably contacts or supports implant 103 and is anchored to surrounding bone or other tissue. The positioning means can also consist of a putty or gel which is packed around the implant 103 to maintain it in position while bone grows into the putty or gel and to the implant or until the putty or gel sets up. Once bone ingrowth secures implant 103 in its desired position, the collar or template which is used to support the implant is removed or is resorbed. Resorption of the collar or implant can occur according to the natural physiological process of the body or can be triggered and/or facilitated by external means such as heat, electricity, enzymes injected into tissue, etc.

By way of further example of the template just referred to, an implant to replace a missing first molar in the lower jaw of a patient is carried out as follows. First, the space between the second premolar and the second molar which bounded the missing first molar may be laser scanned or an impression taken to define the space so that the shape and dimension of the tooth which will fill the space can be defined. An impression is taken of the lower teeth and a plaster model of the lower teeth is made using well known molding techniques. This plaster model, as does the patient's mouth, includes on open spot which at one time was occupied by the patient's missing first molar. A model is made of the artificial tooth which will be mounted on the implant. The model is properly positioned in the open spot in the plaster model and a impression is made of the plaster model using plaster, plastic or any other desired material. This plastic model will fit over and conform to the lower teeth in the patient's mouth. An opening is formed through the plastic model and an externally threaded screw or other attachment means is attached through and extends downwardly from the plastic model so that the implant which will be utilized in the mouth of the patient can be detachably secured to the externally threaded screw. The externally threaded screw positions the implant in the exact desired orientation, both laterally and vertically, with respect to the plastic model and with respect to the opening formed in bone in the patient's mouth (or with respect to bone in the patient's mouth on which the implant is set). An oversized opening 27 (FIG. 3) is drilled in the alveolar bone. The bottom of the opening is prepacked with a selected amount of hydroxyapatite or other composition. The implant 11 is threaded onto the externally threaded screw in the plastic model and the plastic model is fit over the crowns of the patient's lower teeth to force the implant 11 into the opening 27 and force the hydroxyapatite composition up and around the implant 11. Openings can be formed in and through the plastic model to permit hydroxyapatite composition to be added to or removed from opening 27. Or, in the event implant 11 is simply coated with a bone or tissue growth factor, openings need not be formed through the plastic model to permit access to opening 27 because the plastic model positions the implant 11 in the exact desired location in opening 27 and maintains the implant 11 in that position until the tissue growth factor causes an outgrowth of new bone from opening 27 which contacts and anchors implant 11 in position. The coating of bone or tissue growth factor can occur just prior to insertion of the implant, after the implant is inserted, or well prior to insertion of the implant. After the implant 11 is anchored by the growth of new bone toward the implant, the externally threaded screw is turned out of the implant, the plastic model is removed and an artificial tooth can be threaded into or otherwise attached to the anchored implant 11. After (of before, if desired) the artificial tooth is attached to implant 11, a tissue growth factor can be applied around the implant to the surface of the implant, to the surface of bone around implant 11, or to gum tissue to promote the growth of gum tissue over the surface of the bone and adjacent the artificial tooth.

Growth factors can be utilized to induce the growth of "hard tissue" or bone and "soft tissues" like ectodermal and mesodermal tissues. As used herein, the term growth factor encompasses compositions and living organisms which promote the growth of hard tissue, such as bone, or soft tissue in the body of a patient. The compositions include organic and inorganic matter. The compositions can be genetically produced or manipulated. The living organisms can be bacteria, viruses, or any other living organism which promote tissue growth. By way of example and not limitation, growth factors can include platelet-derived growth factor (PDGF), epidermal growth factor (EGF), fibroblast growth factor (acidic/basic)(FGF a,b), interleukins (IL's), tumor necrosis factor (TNF), transforming growth factor (TGF-B), colony-stimulating factor (CSF), osteopontin (Eta-1 (OPN), platelet-derived growth factor (PDGF), interferon (INF), bone morphogenic protein 1 (BMP-1), and insulin growth factor (IGF). Recombinant and non-recombinant growth factors can be utilized as desired. Bacteria or viruses can, when appropriate, be utilized as growth factors. For example, there is a bacterial hydrophilic polypeptide that self-assembles into a nanometer internal diameter pore to build a selective lipid body. Various enzymes can be utilized for the synthesis of peptides which contain amino acids that control three-dimensional protein structure and growth. Growth factors can be applied in gels or other carriers which regulate the rate of release of the growth factors and help maintain the growth factors, and the carrier, at a desired location in the body. Time release capsules, granules, or other carriers containing growth factor can be activated by tissue pH, by enzymes, by ultrasound, by electricity, by heat, by selected in vivo chemicals or by any other selected means to release the growth factor. The carrier can be resorbable or non-resorbable. Or, the growth factor itself can be activated by similar means. Either the carrier or the growth factor can mimic extracellular fluid to control cell growth, migration, and function. The growth factor can be administered orally, systemically, in a carrier, by hypodermic needle, through the respiratory tract, or by any other desired method. The growth factor can also be administered into a capsule or other man-made composition or structure placed in the body. While administration of the growth factor is presently usually localized in the patient's body, circumstances may arise where it is advantageous to distribute a growth factor throughout the patient's body in uniform or non-uniform concentrations. An advantage to growth factors is that they can often, especially when in capsule form or in some other containment system, be inserted to a desired site in the body by simply making a small incision and inserting the growth factor. The making of such a small incision comprises minor surgery which can often be accomplished on an out-patient basis. The growth factors can be multifactorial and nonspecific.

A variety of collagen materials can be used alone and in combination (Types 1 to 12) to form a containment sock, pocket or other structure for a growth factor, which structure may have useful features of controlled degradation and porosity for tissue reconstruction. Other known naturally occurring materials such as biopolymers, crosslinked protein scaffolds, and gels can be used alone or in combination with each other or with any other material to form a containment system for hydroxyapatite or other tissue augmentation materials. A containment pocket or other structure can be formed with synthetic organic materials such as polymers or plastics, with natural inorganic materials (e.g., hydroxyapatite and other ceramics), with organic materials (e.g., biopolymers), or with synthetic inorganic materials.

Possible polymers usable in a pocket or other containment structure constructed in accordance with the invention include, without limitation, poly (Amides), poly(Esters), poly(Orthoesters), poly(Anhydrides), poly (Ureas), poly(Orthoesters), poly(Anhydrides), poly(Ureas), poly(Alkyl 2-Cyanoacrylates), poly(Dihydropyrans), poly(Acetals), poly(Phosphazenes), and poly(Dioxinones). Each of the foregoing polymers is biodegradable in natural systems by undergoing a hydrolytic, enzymatic, or other breakdown or degradation and, as such, is capable of providing biodegradable matrices, scaffolds and other useful structures of a containment structure. Examples of biodegradable polyamides include glutamic acid, glutamic acid/leucine, biodegradable nylon, glutamic acid/ethyl glutamate, hydroxyalkyl-L-glutamine, and collagen. Examples of biodegradable polyesters include D, L lactic acid, glycolic acid/lactic acid, L-lactic acid, caprolactone/D,L lactic acid, diglycolic acid/transcyclonhexanedimethanol, and polyesterhydrogels.

In one embodiment of the packing material 102 used in the invention, hydroxyapatite is mixed with a biodegradable polymer, with or without a growth factor impregnated therein, to provide a composition which resists penetration by epithelial tissues but which promotes growth of adjacent bone or soft tissue structure.

In a further embodiment of the invention, a pocket or other containment structure is fabricated from a microporous material containing a drug or other agent in its pores which promotes the growth of living tissue. The pore sizes can be in the range of 25 to 400 microns, or can have any desired size. The containment structure can be positioned in an opening 101, adjacent selected soft tissue or bone, or at any other location in the patient's body.

In another embodiment of the invention, hydroxyapatite or another tissue augmentation material is mixed with a material to produce a mixture which is sensitive to ultraviolet light and which hardens and sets after being dispensed at a desired location intermediate the tissue and underlying bone. UV light is delivered by fiber optic means to the location at which the augmentation material is dispensed intermediate tissue and underlying bone. The UV light promotes the hardening or setting up of the tissue augmentation material.

In still another embodiment of the invention, a volume of tissue augmentation material is provided with a coating which resists migration from the tissue augmentation material of tissue augmentation drugs or other growth factors or materials. The coating can be biodegradable and break down over time.

The hydroxyapatite (HA) and hydroxyapatite cement (HAC) compositions which can be utilized to pack around implants in accordance with the invention are inorganic, crystalline materials. The hexagonal rhombic prism structure and calcium and phosphate composition of HA's and HAC's are very similar to the natural ceramic hydroxyapatite mineral that makes up the inorganic portion of bone and teeth. HA's and HAC's are bioactive and interact with bone and teeth by forming a direct physicochemical bond with these hard tissues. Consequently, HA's and HAC's are osteoconductive and initiate bone ingrowth. HA's and HAC's can also harbor osteoinductive material like osteocalcin which helps form new bone cells. A distinct advantage of HAC's is that they can, while still in a relatively low viscosity state, be interposed between an implant and opening in the bone to readily conform to implant and bone surfaces. Neither HAC's or HA's generate any appreciable heat when used to pack around an implant. HAC's and HA's can be mixed with bodily fluids.

HAC's, HA's, growth factor compositions, and other packing compositions used to pack around an implant can be formulated to expand after being inserted intermediate an implant and surrounding bone. Such expansion is advantageous because after an opening is cut in bone, the bone adjacent the opening tends to shrink "away" from the opening, enlarging the opening. By way of example, an HAC packing composition can be formulated to expand by intermixing a gas generating material or a material with a thermal coefficient of expansion with the packing composition. The gas generating material forms pores in the packing composition and causes it to expand. The gas generated is preferably carbon dioxide, nitrogen, or another inert gas is preferred. The gas generating or expandable material can be resorbable. If desired, the packing composition can be aerated with a gas before it is inserted in an opening to anchor an implant in place. Polyethylene has a coefficient of thermal expansion of about 0.00018 per degree Centigrade. Polyethylene or another polymer material with a preferred coefficient of thermal expansion can be utilized as a component in the packing composition. Or, the packing composition can include a liquid component which expands when the liquid component sets and solidifies.

In one embodiment of the invention, a dental implant and crown are designed to custom fit in the alveolar bone and efficiently dissipate occlusal stress generated during use of the crown to chew food. Implants other than dental implants can also be designed using the following principles.

A ruler, X-ray, laser scanner, impressions of the teeth and jaws, or other means are used to define the shape and dimension of the space to be occupied by the artificial crown which is attached to the implant and to define the shape and dimension of the alveolar bone in or on which the implant is to be positioned. A force diagram can be generated which defines how the roots of each original tooth in the mouth of an individual dissipate the stresses generated on the tooth during chewing and/or biting. Similarly, a force diagram can be generated defining an optimal root design for uniformly dissipating stress into alveolar bone, for dissipating more stress into stronger areas of the alveolar bone, etc. Such an optimal root design is ordinarily arrived at with the use of a computer and is important because many dental problems derive from the interaction of teeth with bone surrounding the teeth. The quality of the bone adjacent teeth varies. Some bone can withstand occlusal stress better than other bone. Some areas of the jaw have more alveolar bone adjacent to and supporting a tooth than do other areas of the jaw. Another factor which can be utilized to determine the optimal shape and dimension of the implant (and crown) is the material used to fabricate the implant.

An eight foot long two inch by four inch piece of lumber better resists a force which is applied perpendicular to the length of the lumber and to a two inch side of the lumber than it resists the same force applied to a four inch side of the lumber and perpendicular to the length of the lumber. Similarly, the orientation of an implant root with respect to the surrounding bone can have a bearing on the ability of the root and the implant to resist a force vector which is applied to the implant at a particular point and at a particular orientation. Therefore, the orientation of the roots of the implant is another factor which can be taken into consideration by a computer in designing the optimal implant. Still another factor is the shape and position of tooth (or teeth) which opposes and will contact the crown on the implant after the implant and crown are anchored in alveolar bone.

In the dental implant art, the "Theory of Available Bone" teaches that implants are customized to fit in existing bone. The preferred method of the invention directly contradicts the Theory of Available Bone because the method of the invention teaches optimizing the effectiveness of an implant by first defining the optimal shape and dimension and the density or other physical properties of the bone which should be available to anchor the implant. In the method of the invention, if a sufficient volume of bone is not available, additional bone volume is generated by packing HA, HAC or some other material on existing bone to generate new bone, by using growth factors to generate new bone, or by using any other desired procedure to generate new bone. If the density of the existing bone is not sufficient, existing bone can be removed and replaced with HA, HAC, or another desired composition which will have the desired density or other physical properties or which will cause new bone to grow which has the desired density or other physical properties. HAC can form bone consisting of about 77% by weight mineral composition. This is denser than natural bone and can be particularly desirable in forming new bone in the posterior bone areas of the mouth. The bone in the posterior areas of the mouth supports the molars. Such bone typically is less dense than the bone in the anterior areas of the mouth. Bone in the anterior areas of the mouth supports incisors. In addition, if the existing bone volume is too great, bone can be removed; for example, a bone spur could be removed. Consequently, the method of the invention propounds a "Theory of Optimal Bone-Optimal Implant" design and implementation in which existing bone structure can be altered and the design of each implant can, if appropriate, differ from the design of the other implants in a patient's mouth in order to insure that a implant is formed which effectively distributes the occlusal forces generated on the implant and bone during use of the teeth. Any desired set of criteria or parameters can be used in defining the desired volume, density, and other physical properties of the bone used to support an implant. For example, but not by way of limitation, the volume of bone typically will approximate the volume of the original bone structure which is (or was) present in the mouth when the patient is a young adult. Such bone volume is readily measured or, in the event portions of the original bone structure have been lost, can be readily approximated. The desired density of the bone typically presently will be at least equal to the density of the original bone structure.

A computer can also be utilized to determine the position of the implant at which the implant optimally distributes stresses into surrounding bone. The optimal position of the implant can be determined based upon selected factors included, but not limited to, the morphology of the surrounding alveolar bone, the size and stability of adjacent teeth, etc. For example, once the shape and dimension of an implant is determined, the implant may better distribute stress if it is positioned in (or on) alveolar bone closer to a first adjacent tooth than to a second adjacent tooth because the quality of bone is better near the first adjacent tooth.

The shape and dimension of the crown can depend on factors including, but not limited to, the type of tooth (a molar has more cusps than an incisor), the size of the space in the patient's mouth in which the crown must fit, and the material used to fabricate the crown (a stronger material might enable portions of the crown to be smaller than if a weaker material is used).

After the shape and dimension of the implant and crown are defined, the implant and crown can be manufactured using computerized equipment. A computerized lathe system could, for example, be used to cut the implant from a piece of metal and to cut, mold, or otherwise form the crown which is secured to the implant. Or, the implant and crown can be produced utilizing any desired conventional production methods. After the implant and crown are produced, the implant is anchored at the desired position in the alveolar bone using any of the procedures earlier described. For example, on opening can be formed in the alveolar bone, the implant inserted in the opening, and HA or other material packed around the implant to anchor the implant in the opening. The crown can be attached to the implant before or after the implant is secured in the alveolar bone.

Having described my invention in such terms as to enable those skilled in the art to understand and practice it, and having described the presently preferred embodiments thereof,

I claim:

1. A method of anchoring an implant in the bone of a patient, comprising the steps of
   (a) forming an opening in the bone, said opening including a peripheral wall circumscribing and enclosing an open space;
   (b) inserting an implant in said opening, said implant comprising a body and a head supported on said body, said implant only partially occupying said open space and being freely movable from side-to-side in said open space to contact and move away from said peripheral wall, a portion of said open space being unoccupied by said implant;
   (c) fixing said implant in a selected position in said opening by filling said portion of said open space with a bone inducing composition, said composition including a tissue growth factor and hardening to form a structure which fixes said implant in position in said opening, said composition
      (i) extending from at least a portion of said wall to said implant and contacting said wall and said implant to fix said implant in position in said opening,
      (ii) extending from said bottom of said body upwardly over said body and said head of said implant, and
      (iii) facilitating the formation of new bone in said space in said opening which is filled with said composition;
   (d) waiting for said composition to harden; and, (e) waiting for bone to form in said space in said opening which is filled with said composition.

2. The method of claim 1 wherein
   (a) in step (c), said space in said opening which is unoccupied by said implant is filled with a porous composition which hardens into a structure which has pores and which permits the ingrowth of bone into said pores; and,
   (b) step (e) comprises waiting for bone to form in said pores.

3. The method of claim 1 wherein
   (a) in step (c), said space in said opening which is unoccupied by said implant is filled with a composition which is resorbed by the body and promotes the formation of bone in said space in said opening which is unoccupied by said implant; and,
   (b) step (e) comprises waiting for said composition to be resorbed by the body and for bone to be formed in said space in said opening which is unoccupied by said dental implant.

4. A method of anchoring an implant in the bone of a patient, comprising the steps of
   (a) forming an opening in the bone, said opening including a peripheral wall circumscribing and enclosing an open space;
   (b) inserting an implant in said opening, said implant comprising a body and a head supported on said body, said implant only partially filling said open space and being freely movable in said opening, a portion of said open space being unoccupied by said implant;
   (c) tilting and positioning said implant in said open space;
   (d) filling said portion of said open space with a malleable composition to fix said implant in a selected position in said opening, said composition
      (i) subsequently hardening to form a structure which fixes said implant in position in said opening,
      (ii) extending from said wall to said implant and contacting said wall and said implant to fix said implant in position in said opening,
      (iii) extending from said bottom of said body upwardly over said body and said head of said implant, and
      (iv) including a bone growth factor and facilitating the formation of new bone in said space in said opening which is filled with said malleable composition;
   (e) waiting for said composition to harden; and,
   (f) waiting for bone to form in said space in said opening which is filled with said hardened composition.

5. A method of anchoring an implant in the bone of a patient, comprising the steps of
   (a) forming an opening in the bone, said opening including a peripheral wall circumscribing and enclosing an open space;
   (b) inserting an implant in a selected position in said opening, said implant comprising a body and a head supported on said body, said implant only partially filling the space in said opening and spaced apart from at least a portion of said peripheral wall;
   (c) inserting bone growth factor in said opening;
   (d) maintaining said implant in said selected position in said opening until said bone growth factor causes new bone growth in said opening.

6. The method of claim 5 wherein in step (a) said opening is sized to be larger than said implant such that said implant is loose in said opening after insertion in said opening in step (b).

7. A method of anchoring a dental implant in the alveolar bone of a patient, comprising the steps of
   (a) forming an opening in the alveolar bone, said opening including a peripheral wall circumscribing and enclosing an open space;
   (b) inserting an implant in said opening, said implant comprising a body and a head supported on said body and adapted to support an artificial tooth, said implant only partially filling said open space and being freely movable in said opening, a portion of said open space being unoccupied by said implant;
   (c) filling said portion of said open space with a malleable composition to fix said implant in a selected position in said opening, said composition including a growth factor and
      (i) subsequently hardening to form a structure which fixes said implant in position in said opening,
      (ii) permitting said implant to be tilted to deform said malleable composition and reposition said implant,
      (iii) extending from said wall to said implant and contacting said wall and said implant to fix said implant in position in said opening,
      (iv) extending from said bottom of said body upwardly over said body and said head of said implant, and
      (v) facilitating the formation of new bone in said portion of said open space which is filled with said malleable composition;
   (d) tilting said implant to reposition said implant in said packed malleable composition;
   (e) repacking said malleable composition;
   (f) waiting for said composition to harden; and,
   (g) waiting for bone to form in said space in said opening which is filled with said hardened composition.

8. The method of claim 7, wherein in step (c), said portion of said open space is completely filled with a resorbable bone inducing composition to fix said implant in a selected position in said opening, said composition hardening to form a structure which fixes said implant in position in said opening, said composition
   (i) extending from at least a portion of said wall to said implant and contacting said wall and said implant to fix said implant in position in said opening,
   (ii) extending from said bottom of said body upwardly over said body and said neck of said implant, and
   (iii) facilitating the formation of new bone in said space in said opening which is filled with said composition; said unoccupied portion of said opening is filled with a bone inducing resorbable composition which hardens to maintain said implant in fixed position in said opening.

* * * * *